US008034826B2

(12) United States Patent
Hutchinson et al.

(10) Patent No.: US 8,034,826 B2
(45) Date of Patent: Oct. 11, 2011

(54) CYCLOALKANE[B]AZAINDOLE ANTAGONISTS OF PROSTAGLANDIN $D_2$ RECEPTORS

(75) Inventors: John Howard Hutchinson, La Jolla, CA (US); Brian Andrew Stearns, San Diego, CA (US); Jill Melissa Scott, Cardiff, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 60 days.

(21) Appl. No.: 12/613,424

(22) Filed: Nov. 5, 2009

(65) Prior Publication Data

US 2010/0113503 A1 May 6, 2010

Related U.S. Application Data

(60) Provisional application No. 61/112,044, filed on Nov. 6, 2008.

(51) Int. Cl.
*A61K 31/437* (2006.01)
*C07D 471/04* (2006.01)
*A61P 11/00* (2006.01)
*A61P 37/08* (2006.01)
*A61P 29/00* (2006.01)

(52) U.S. Cl. .......................................... 514/292; 546/87

(58) Field of Classification Search .................... 546/87; 514/292

See application file for complete search history.

(56) References Cited

U.S. PATENT DOCUMENTS

| | | | |
|---|---|---|---|
| 5,223,517 | A | 6/1993 | Muller et al. |
| 7,144,913 | B2 | 12/2006 | Wang et al. |
| 2003/0096813 | A1 | 5/2003 | Cao et al. |
| 2005/0171143 | A1 | 8/2005 | Tanimoto et al. |
| 2005/0272756 | A1 | 12/2005 | Leblanc et al. |
| 2007/0191416 | A1 | 8/2007 | Fecher et al. |
| 2009/0186923 | A1 | 7/2009 | Armer et al. |

FOREIGN PATENT DOCUMENTS

| | | | |
|---|---|---|---|
| EP | 1170594 | A2 | 1/2002 |
| EP | 1505061 | A1 | 2/2005 |
| GB | 2465062 | B | 4/2011 |
| JP | 2004-182657 | A | 7/2004 |
| WO | WO-2007-070892 | A2 | 6/1997 |
| WO | WO-02-085909 | A1 | 10/2002 |
| WO | WO-03-062200 | A2 | 7/2003 |
| WO | WO-2004-035543 | A1 | 4/2004 |
| WO | WO-2004-058164 | A2 | 7/2004 |
| WO | WO-2004-096777 | A1 | 11/2004 |
| WO | WO-2005-040114 | A1 | 5/2005 |
| WO | WO-2005-044260 | A1 | 5/2005 |
| WO | WO-2005-095397 | A1 | 10/2005 |
| WO | WO-2006-052798 | A2 | 5/2006 |
| WO | WO-2006-052798 | A3 | 5/2006 |
| WO | WO-2006-070325 | A2 | 7/2006 |
| WO | WO-2007-019675 | A1 | 2/2007 |
| WO | WO-2007-037187 | A1 | 4/2007 |
| WO | WO-2007-107772 | A1 | 9/2007 |
| WO | WO-2007-144127 | A1 | 12/2007 |
| WO | WO-2008-017989 | A1 | 2/2008 |
| WO | WO-2008-019357 | A2 | 2/2008 |
| WO | WO-2008-137027 | A2 | 11/2008 |
| WO | WO-2008-156780 | A1 | 12/2008 |
| WO | WO-2009-004379 | A1 | 1/2009 |
| WO | WO-2009-044147 | A1 | 4/2009 |
| WO | WO-2009-049021 | A1 | 4/2009 |
| WO | WO-2009-063202 | A2 | 5/2009 |
| WO | WO-2009-063215 | A2 | 5/2009 |
| WO | WO-2009-140642 | A2 | 11/2009 |
| WO | WO-2010-008864 | A2 | 1/2010 |
| WO | WO-2010-085820 | A2 | 7/2010 |
| WO | WO-2010-085820 | A3 | 7/2010 |
| WO | WO-2011-014587 | A2 | 2/2011 |
| WO | WO-2011-014588 | A2 | 2/2011 |

OTHER PUBLICATIONS

Kelly et al., Journal of the chemical society [section] C: organic (1970), (2), 303-7.*

Blache et al., Compared Reactivity of Heterocyclic Enaminones: Photochemical and Palladium Catalyzed Synthesis of 6,7,8,9-Tetrahydro-5H-pyrido[3,2-b]indol-9-ones, J. Org. Chem. 62(24):8553-8446 (1997).

PCT/US09/063439 Search Report dated Jun. 28, 2010.

PCT/US 09/063438 Search Report dated Jun. 28, 2010.

Arima and Fukuda, "Prostaglandin D2 Receptors DP and CRTH2 in the Pathogenesis of Asthma," Curr. Mol. Med. 8:365-375 (2008).

Hata and Breyer, "Pharmacology and signaling of prostaglandin receptors: Multiple roles in inflammation and immune modulation," Pharmacol. Ther. 103:147-166 (2004).

Kostenis and Ulven, "Emerging roles of DP and CRTH2 in allergic inflammation," Trends Mol. Med. 12(4):148-158 (2006).

Medina and Liu, "PGD2 Antagonists," Annual Reports Med. Chem. 41:221-235 (2006).

Pettipher et al., "Antagonism of the prostaglandin D2 receptors DP1 and CRTH2 as an approach to treat allergic diseases," Nature Reviews/Drug Discovery 6:313-325 (2007).

Stearns et al., "Novel tricyclic antagonists of the prostaglandin D2 receptor DP2 with efficacy in murine model of allergic rhinitis," Bioor. Med. Chem. Letters 19:4647-4651 (2009).

Tirouvanziam et al., "Profound functional and signaling changes in viable inflammatory neutrophils homing to cystic fibrosis airways," PNAS 105(11):4335-4339 (2008).

Ulven and Kostenis, "Targeting the Prostaglandin D2 Receptors DP and CRTH2 for Treatment of Inflammation," Curr. Topics Med. Chem. 6:1427-1444 (2006).

GB0919199.0 Search Report dated Nov. 18, 2009.

Crosignani et al., "Discovery of a New Class of Potent, Selective, and Orally Bioavailable CRTH2 (DP2) Receptor Antagonists for the Treatment of Allergic Inflammatory Diseases," J Med Chem 51:2227-2243 (2008).

(Continued)

*Primary Examiner* — D M Seaman
*Assistant Examiner* — Niloofar Rahmani
(74) *Attorney, Agent, or Firm* — Wilson Sonsini Goodrich & Rosati

(57) ABSTRACT

Described herein are compounds that are antagonists of $PGD_2$ receptors. Also described are pharmaceutical compositions that include the compounds described herein, and methods of using such antagonists of $PGD_2$ receptors, alone or in combination with other compounds, for treating respiratory, cardiovascular, and other $PGD_2$-dependent or $PGD_2$-mediated conditions or diseases.

12 Claims, No Drawings

OTHER PUBLICATIONS

Evans and Hutchinson, "Seeing the future of bioactive lipid drug targets," Nature Chem Biol 6:476-479 (2010).

Kim and Luster, "Regulation of Immune Cells by Eicosanoid Receptors," TheScientificWorldJournal 7:1307-1328 (2007).

Ly and Bacon, "Small-molecule CRTH2 antagonists for the treatment of allergic inflammation: an overview," Expert Opin Investig Drugs 14(7):769-773 (2005).

Pettipher and Hansel, "Antagonists of the Prostaglandin D2 Receptor CRTH2," Drug News Perspect 21 (6):317-322 (2008).

Pettipher, R., "The roles of the prostaglandin D2 receptors DP1 and CRTH2 in promoting allergic responses," Br J Pharmacol 153:S191-S199 (2008).

Prieto et al., "Racemization in Suzuki Couplings: A Quantitative Study Using 4-Hydroxyphenylglycine and Tyrosine Derivatives as Probe Molecules," J Org Chem 72:1047-1050 (2007).

Sandham et al., "7-Azaindole-3-acetic acid derivatives: Potent and selective CRTH2 receptor antagonists," Bioorg Med Chem Ltrs 19:4794-4798 (2009).

Sandig et al., "Contrary prostaglandins: the opposing roles of PGD2 and its metabolites in leukocyte function," J Leukocyte Biol 81:372-382 (2007).

Scott et al., "Discovery and optimization of a biphenylacetic acid series of prostaglandin D2 receptor DP2 antagonists with efficacy in a murine modelof allergic rhinitis," Bioorg Med Chem Ltrs accepted Jan. 6, 2011, DOI 10.1016/j.bmcl.2011.01.024.

Stebbins et al., "Therapeutic efficacy of AM156, a novel prostanoid DP2 receptor antagonist, in murine models of allergic rhinitis and house dust mite-induced pulmonary inflammation," Eur J Pharmacol 638:142-149 (2010).

Stebbins et al., "Pharmacological Blockade of the DP2 Receptor Inhibits Cigarette Smoke-Induced Inflammation, Mucus Cell Metaplasia, and Epithelial Hyperplasia in the Mouse Lung," J Pharmacol Exp Therapeutics 331 (3):764-775 (2010).

Stebbins et al., "DP2 Receptor Antagonists: Novel Therapeutic Target for COPD," Mol Cell Pharmacol 2(3):89-96 (2010).

Stock et al., "Sodium [2'-[(cyclopropanecarbonyl-ethyl-amino)-methy1]-4'(6-ethoxy-pyridin-3-yl)-6-methoxy-biphenyl-3-yl]-acetate (AM432):A potent, selective prostaglandin D2 receptor antagonist," Bioorg Med Chem Ltrs 21:1036-1040 (2011).

Takeshita et al., "CRTH2 is a prominent effector in contact hypersensitivity-induced neutrophil inflammation," Int Immunol 16(7):947-959 (2004).

Torisu et al., "Discovery of new chemical leads for prostaglandin D2 receptor antagonists," Bioorg Med Chem Ltrs 14:4557-4562 (2004).

Ulven and Kostenis, "Minor Structural Modifications Convert the Dual TP/CRTH2 Antagonist Ramatrobin into a Highly Selective and Potent CRTH2 Antagonist," J Med Chem 48(4):897-900 (2005).

PCT/US09/44219 International Search Report and Written Opinion mailed Jan. 19, 2010.

PCT/US09/44219 International Preliminary Examination Report mailed Nov. 17, 2010.

PCT/US09/44219 International Preliminary Report on Patentability mailed.

PCT/US09/48327 International Search Report and Written Opinion mailed Jan. 29, 2010.

PCT/US09/48327 International Preliminary Examination Report mailed Jan. 13, 2011.

PCT/US09/48327 International Preliminary Report on Patentability mailed.

Srinivas et al., "Biaryl amino acid templates in place of D-Pro-L-Pro in cyclic beta-hairpin cationic antimicrobial peptidomimetics," Organic & Biomolecular Chemistry 5(19):3100-3105 (2007).

PCT/US10/43599 Search Report and Written Opinion mailed Apr. 28, 2011.

PCT/US10/43598 Search Report and Written Opinion mailed Apr. 20, 2011.

* cited by examiner

CYCLOALKANE[B]AZAINDOLE ANTAGONISTS OF PROSTAGLANDIN $D_2$ RECEPTORS

RELATED APPLICATIONS

This application claims the benefit of U.S. provisional patent application No. 61/112,044 entitled "CYCLOALKANE[B]AZAINDOLE ANTAGONISTS OF PROSTAGLANDIN $D_2$ RECEPTORS" filed on Nov. 6, 2008, which is incorporated by reference in its entirety.

FIELD OF THE INVENTION

Described herein are compounds, methods of making such compounds, pharmaceutical compositions comprising such compounds, and methods of using such compounds to treat, prevent or diagnose diseases or conditions associated with prostaglandin $D_2$.

BACKGROUND OF THE INVENTION

Prostaglandins have a diverse range of activities and have a well recognized role in pain and inflammation. Prostaglandin $D_2$ ($PGD_2$) is produced by mast cells, macrophages and Th2 lymphocytes in response to local tissue damage as well as allergic inflammation in diseases such as asthma, rhinitis, and atopic dermatitis. $PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$).

SUMMARY OF THE INVENTION

Presented herein are compounds, pharmaceutical compositions, and methods, for (a) diagnosing, preventing, or treating allergic and non-allergic inflammation, (b) mitigating adverse signs and symptoms that are associated with inflammation, and/or (c) controlling immunological, proliferative disorders. These disorders may arise from one or more of a genetic, iatrogenic, immunological, infectious, oncological, toxic, surgical, and/or traumatic etiology. In one aspect, the methods, compounds, pharmaceutical compositions, and medicaments described herein comprise an antagonist of $PGD_2$ receptors. In one aspect, the methods, compounds, pharmaceutical compositions, described herein comprise an antagonist of $DP_2$.

In one aspect provided herein are compounds of Formula (I), (II), (III) and (IV), pharmaceutically acceptable salts, pharmaceutically acceptable prodrugs, N-oxides and pharmaceutically acceptable solvates thereof, which are antagonists of $DP_2$, and are used to treat mammals suffering from one or more $PGD_2$-dependent conditions or diseases, including, but not limited to, asthma, rhinitis, allergic conjunctivitis, atopic dermatitis, chronic obstructive pulmonary disease (COPD), pulmonary hypertension, interstitial lung fibrosis, arthritis, allergy, psoriasis, inflammatory bowel disease, adult respiratory distress syndrome, myocardial infarction, aneurysm, stroke, cancer, wound healing, endotoxic shock, pain, inflammatory conditions, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, angioedema, anaphylaxia, chronic cough and Churg Strauss syndrome.

In one aspect, provided is a compound having the structure of Formula (I), or pharmaceutically acceptable salt, or N-oxide thereof:

Formula (I)

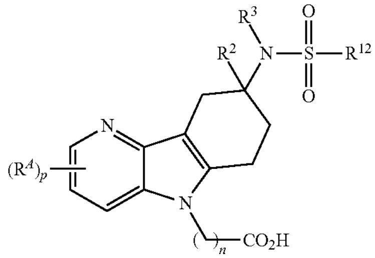

wherein, each $R^A$ is independently H, F, Cl, Br, I, —CN, —$NO_2$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;

$R^2$ is H or $C_1$-$C_4$alkyl;

$R^3$ is H, $C_1$-$C_4$alkyl, $C_1$-$C_4$fluoroalkyl or -$L^3$-$X^3$;

-$L^3$- is —$C_1$-$C_4$alkylene-;

—$X^3$ is H, F, —CN, $CO_2R^{13}$, —C(═O)N($R^{13}$)$_2$, tetrazolyl, or —OH;

$R^{12}$ is $C_1$-$C_6$alkyl, $C_1$-$C_6$haloalkyl, $C_1$-$C_6$heteroalkyl, a substituted or unsubstituted phenyl, a substituted or unsubstituted naphthyl, a substituted or unsubstituted monocyclic heteroaryl or a substituted or unsubstituted bicyclic heteroaryl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, $C_1$-$C_4$alkyl, $C_1$-$C_4$fluoroalkyl, $C_1$-$C_4$alkoxy, $C_1$-$C_4$fluoroalkoxy, or $C_1$-$C_4$heteroalkyl;

each $R^{13}$ is independently H, $C_1$-$C_4$alkyl, or a substituted or unsubstituted phenyl;

n is 1 or 2; p is 0, 1 or 2.

Compounds of Formula (I) include compounds of Formula (II), Formula (III) and Formula (IV).

In one aspect, presented herein are the compounds of Formula (I), (II), (III) and (IV), presented in Table 1, or pharmaceutically acceptable salts, pharmaceutically active metabolites, pharmaceutically acceptable prodrugs, N-oxides or pharmaceutically acceptable solvates thereof.

Compounds of Formula (I), (II), (III) and (IV), are antagonists of $DP_2$.

In one aspect, provided herein are pharmaceutical compositions comprising a therapeutically effective amount of a compound of Formula (I), (II), (III) or (IV). In some embodiments, the pharmaceutical compositions comprise at least one inactive pharmaceutically acceptable inactive ingredient selected from excipients, diluents, and carriers.

In certain embodiments, presented herein are methods for treating a $PGD_2$-dependent condition or disease in a mammal comprising administering to the mammal a therapeutically effective amount of a compound of Formula (I), (II), (III) or (IV).

In another aspect, compounds of Formula (I), (II), (III) or (IV) are used to treat or prevent inflammatory diseases or conditions. Inflammatory conditions include, but are not limited to, asthma, rhinitis, chronic obstructive pulmonary disease, pulmonary hypertension, interstitial lung fibrosis, atherosclerosis, aortic aneurysm, myocardial infarction, and stroke.

In a specific aspect, provided herein is a method for treating asthma in a mammal comprising administering a therapeutically effective amount of a compound provided herein to the mammal in need.

In another aspect, compounds of Formula (I), (II), (III) or (IV) are used to treat or prevent immunological disorders, including, but are not limited to, allergy or to excessive or inappropriate response to an endogenous or exogenous antigen. In certain embodiments, the immunological disorder is characterized by immune dysregulation that is not accompanied by inflammation.

In additional aspects, such diseases or conditions are iatrogenic and increases in, or abnormal localization of, $PGD_2$ is induced by other therapies or medical or surgical procedures. In other embodiments, the $PGD_2$-dependent or $PGD_2$ mediated condition or disease is caused by surgery.

In another aspect are methods for treating respiratory diseases or conditions in a mammal comprising administering to the mammal at least once an effective amount of at least one compound of Formula (I), (II), (III) or (IV). In a further embodiment of this aspect, the respiratory disease is asthma. In a further embodiment of this aspect, the respiratory disease includes, but is not limited to, asthma, adult respiratory distress syndrome, allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophilic asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In another aspect compounds described herein are used for treating rhinitis in a mammal. In a further embodiment of this aspect, compounds described herein are used for treating allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In another aspect are methods for treating chronic obstructive pulmonary disease comprising administering to the mammal at least once an effective amount of a compound of Formula (I), (II), (III) or (IV). In a further embodiment of this aspect, chronic obstructive pulmonary disease includes, but is not limited to, chronic bronchitis and/or emphysema, pulmonary hypertension, interstitial lung fibrosis and/or airway inflammation and cystic fibrosis.

In another aspect are methods for preventing increased mucosal secretion and/or edema in mammals comprising administering to the mammal at least once an effective amount of a compound of Formula (I), (II), (III) or (IV).

In another aspect are methods for preventing eosinophil and/or basophil and/or dendritic cell and/or neutrophil and/or monocyte or Th2 cell recruitment in a mammal comprising administering to the mammal an effective amount of a compound of Formula (I), (II), (III) or (IV).

In another aspect are methods for treating or preventing ocular inflammation, conjunctivitis, retinitis, scleritis, uveitis, allergic conjunctivitis, vernal keratoconjunctivitis, and papillary conjunctivitis in a mammal comprising administering to the mammal at least once an effective amount of a compound of Formula (I), (II), (III) or (IV).

In another aspect, compounds of Formula (I), (II), (III) and (IV) are used to treat or prevent pain in a mammal.

In another aspect are methods for preventing or treating acute or chronic disorders involving recruitment or activation of eosinophils in a mammal comprising administering to the mammal at least once an effective amount of a compound of Formula (I), (II), (III) or (IV).

In another aspect are methods for treating inflammatory responses of the skin in a mammal comprising administering to the mammal at least once an effective amount of at least one compound of Formula (I), (II), (III) or (IV). Such inflammatory responses of the skin include, by way of example, psoriasis, dermatitis, atopic dermatitis, contact dermatitis, eczema, urticaria, rosacea, bullous disorders, collagenoses, Kawasaki Disease, Sjogren-Larsso Syndrome, wound healing and scarring. In another aspect are methods for reducing psoriatic lesions in the skin, joints, or other tissues or organs, comprising administering to the mammal an effective amount of a compound of Formula (I), (II), (III) or (IV). In another aspect are methods for reducing psoriatic lesions in the skin, joints, or other tissues or organs, comprising administering at least once to the mammal an effective amount of a compound of Formula (I), (II), (III) or (IV).

In a further aspect are methods to modulate the immune response to endogenous or exogenous antigens in a mammal. In a further aspect are methods to treat acute or chronic allergic responses to exogenous substances that have been ingested such as foods (e.g., peanuts) or drugs (e.g., penicillin, non-steroidal anti-inflammatory drugs or the like).

In another aspect is the use of a compound of Formula (I), (II), (III) or (IV) in the manufacture of a medicament for treating an inflammatory disease or condition in a mammal in which the activity of at least one $PGD_2$-associated protein contributes to the pathology and/or symptoms of the disease or condition. In one embodiment of this aspect, the $PGD_2$ pathway protein is DP2. In another or further embodiment of this aspect, the inflammatory disease or conditions are respiratory, cardiovascular, or proliferative diseases or conditions.

"Cardiovascular disease or conditions," refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In any of the aforementioned aspects are further embodiments in which: (a) the effective amount of the compound is systemically administered to the mammal; and/or (b) the effective amount of the compound is administered orally to the mammal; and/or (c) the effective amount of the compound is intravenously administered to the mammal; and/or (d) the effective amount of the compound administered by inhalation; and/or (e) the effective amount of the compound is administered by nasal administration; or and/or (f) the effective amount of the compound is administered by injection to the mammal; and/or (g) the effective amount of the compound is administered topically (dermal) to the mammal; and/or (h) the effective amount of the compound is administered by ophthalmic administration; and/or (i) the effective amount of the compound is administered rectally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered once daily; (ii) the compound is administered twice daily; (iii) the compound is administered in cycles that include daily administration for a period of time followed by at least 1 day without administration; (iv) the compound is administered in cycles that include daily administration for a period of time followed by at least 1 day that includes a dose reduction in the daily amount of compound that is administered.

In any of the aforementioned aspects involving the treatment of $PGD_2$ dependent diseases or conditions are further embodiments comprising administering at least one additional agent in addition to the administration of a compound having the structure of Formula (I), (II), (III) or (IV).

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and Th2 lymphocytes in response to local tissue damage as well as in response allergic inflammation observed in diseases such as asthma, rhinitis, and atopic dermatitis. Exogenous $PGD_2$ applied to bronchial airways elicits many responses that are characteristic of acute asthma.

Activation of $DP_2$ is associated with chemotaxis and activation of Th2 lymphocytes, eosinophils and basophils. $PGD_2$ binds to $DP_2$ and mediates many of its effects through a $G_i$-dependent elevation of intracellular calcium levels and reduction of cyclic AMP. In Th2 lymphocytes, IL4, IL5 and IL13 cytokine production are also stimulated by $DP_2$ activation. These cytokines have been implicated in numerous biological actions including, by way of example only, immunoglobulin E production, airway response, mucous secretion, and eosinophil recruitment.

In the brain and central nervous system, $PGD_2$ is produced and thought to function in pain perception and sleep regulation. In other tissues, $PGD_2$ is produced primarily in immunoglobulin E (IgE) activated mast cells and to a lesser extent, in macrophages, dendritic cells, T helper 2 (Th2) lymphocytes and other leukocytes. In the cell, $PGD_2$ is rapidly metabolized and converted to other downstream effectors including $\Delta^{12}PGJ_2$, $9\alpha 11\beta PGF_2$, 13,14-dihydro-15-keto-$PGD_2$, and 15-deoxy-$\Delta^{12,14}PGD_2$.

Mast-cell-derived $PGD_2$ is produced in high concentrations in response to an allergen challenge. Studies in preclinical species have observed the following features when $PGD_2$ is applied to in vivo preparations, or its overproduction is engineered by genetic manipulation: vasodilatation leading to erythema (flare) and potentiation of oedema (wheal), recruitment of eosinophils and Th2 lymphocytes, modulation of Th2-cytokine production, bronchoconstriction.

Injection of $PGD_2$ into human skin has been shown to produce a long lasting erythema, to potentiate the effects of other mediators on induration and leukocyte infiltration in human skin and to enhance oedema formation in rat skin. It is most likely that these effects of $PGD_2$, like those of other vasodilator prostaglandins, are due to an increased blood flow to the inflamed lesion and are, therefore, most likely to be mediated predominantly by the $DP_1$ receptor. Although these observations make it clear that $DP_1$ mediates the vascular effects of $PGD_2$, the capacity of $PGD_2$ to promote the cellular changes associated with inflammation is not due to an action on $DP_1$.

Much of $PGD_2$'s pro-inflammatory activity is through interaction with $DP_2$. $DP_2$ is a G-protein coupled receptor and is typically highly expressed in Th2 lymphocytes, eosinophils and basophils. $DP_2$ activation functions to directly activate and recruit Th2 lymphocytes and eosinophils. Activated Th2 lymphocytes produce and secrete inflammatory cytokines including IL4, IL5, and IL13. Despite binding $PGD_2$ with a similar affinity as $DP_1$, $DP_2$ is not structurally related to $DP_1$ and signals through a different mechanism—the effects of $DP_2$ are mediated through Gi-dependent elevation in intracellular calcium levels and reduction in intracellular levels of cyclic AMP. $DP_2$ activation is important in eosinophil recruitment in response to allergic challenge in such tissues as nasal mucosa, bronchial airways, and skin. The application of either $PGD_2$ or selective $DP_2$ agonists both exacerbate and enhance allergic responses in lung and skin. $DP_2$ activation appears to have a crucial role in mediating allergic responses. The use of antagonists of $PGD_2$ activation of the $DP_2$ receptor is an approach to treat the inflammatory component of inflammatory diseases or conditions, respiratory diseases or conditions, allergic diseases or conditions, such as asthma, rhinitis, and dermatitis, among others.

Compounds

Described herein are compounds of Formula (I), Formula (II), Formula (III) and Formula (IV). Also described are pharmaceutically acceptable salts of compounds of Formula (I), Formula (II), Formula (III) and Formula (IV). In some embodiments, the compound of Formula (I), Formula (II), Formula (III) or Formula (IV) is provided as an N-oxide.

Compounds of Formula (I) have the following structure:

Formula (I)

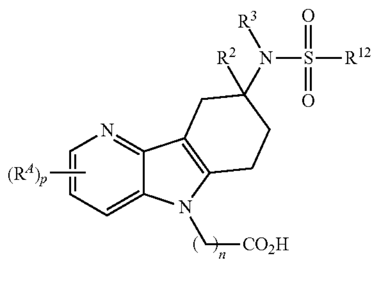

wherein, each $R^A$ is independently H, F, Cl, Br, I, —CN, —$NO_2$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;

$R^2$ is H or $C_1$-$C_4$alkyl;

$R^3$ is H, $C_1$-$C_4$alkyl, $C_1$-$C_4$fluoroalkyl or -$L^3$-$X^3$;

-$L^3$- is —$C_1$-$C_4$alkylene-;

—$X^3$ is H, F, —CN, —$CO_2R^{13}$, —C(=O)N($R^{13}$)$_2$, tetrazolyl, or —OH;

$R^{12}$ is $C_1$-$C_6$alkyl, $C_1$-$C_6$haloalkyl, $C_1$-$C_6$heteroalkyl, a substituted or unsubstituted phenyl, a substituted or unsubstituted naphthyl, a substituted or unsubstituted monocyclic heteroaryl or a substituted or unsubstituted bicyclic heteroaryl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, $C_1$-$C_4$alkyl, $C_1$-$C_4$fluoroalkyl, $C_1$-$C_4$alkoxy, $C_1$-$C_4$fluoroalkoxy, or $C_1$-$C_4$heteroalkyl;

each $R^{13}$ is independently H, $C_1$-$C_4$alkyl, or a substituted or unsubstituted phenyl;

n is 1 or 2;

p is 0, 1 or 2.

For any and all of the embodiments, substituents can be selected from among from a subset of the listed alternatives. For example, in some embodiments, $R^2$ is H or —$CH_3$. In some embodiments, $R^2$ is H.

In some embodiments, $R^3$ is H, —$CH_3$, —$CH_2CH_3$, or —$CH_2CF_3$. In some embodiments, $R^3$ is H or —$CH_3$. In some embodiments, $R^3$ is H. In some embodiments, $R^3$ is —$CH_3$.

In some embodiments, n is 1. In some embodiments, n is 2.

In some embodiments, $R^2$ is H or —$CH_3$; $R^3$ is H or —$CH_3$; n is 1.

In some embodiments, $R^{12}$ is a substituted or unsubstituted phenyl, or a substituted or unsubstituted 6-membered monocyclic heteroaryl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, —$CH_3$, —$CF_3$, —$OCH_3$, or —$OCF_3$. In some embodiments, $R^{12}$ is a substituted or unsubstituted phenyl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, —$CH_3$, —$CF_3$, —$OCH_3$, or —$OCF_3$. In some embodiments, $R^{12}$ is a substituted or unsubstituted phenyl, or a substituted or unsubstituted pyridinyl, where if $R^{12}$ is substituted then $R^{12}$ is substituted with 1 or 2 $R^{14}$. In some embodiments, $R^{12}$ is a substituted or unsubstituted phenyl, where if $R^{12}$ is substituted then $R^{12}$ is substituted with 1 or 2 $R^{14}$. In some embodiments, $R^{12}$ is a substituted or unsubstituted 6-membered monocyclic heteroaryl, where if $R^{12}$ is substituted then $R^{12}$ is substituted with 1 or 2 $R^{14}$.

In some embodiments, $R^2$ is H; $R^{12}$ is a substituted or unsubstituted phenyl, or a substituted or unsubstituted 6-membered monocyclic heteroaryl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, —$CH_3$, —$CF_3$, —$OCH_3$, or —$OCF_3$.

In some embodiments, the compound of Formula (I) has the structure of Formula (II):

Formula (II)

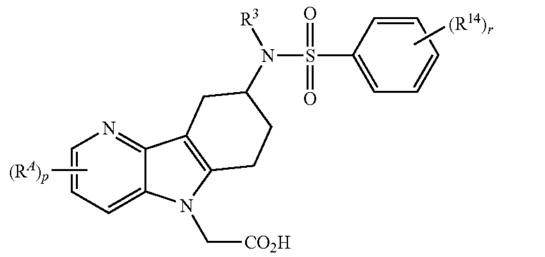

wherein: r is 0, 1 or 2.

In some embodiments, r is 0. In some embodiments, r is 0 or 1. In some embodiments, r is 1 or 2. In some embodiments, r is 1. In some embodiments, r is 2.

In some embodiments, each $R^A$ is independently H, F, Cl, Br, —CN, —$CH_3$, —$CF_3$, —$OCF_3$, or —$OCH_3$.

In some embodiments, p is 0, 1 or 2. In some embodiments, p is 0 or 1. In some embodiments, p is 0. In some embodiments, p is 1.

In some embodiments, each $R^{14}$ is independently H, F, Cl, Br, —CN, —$CH_3$, —$CF_3$, —$OCF_3$, or —$OCH_3$. In some embodiments, r is 1; and $R^{14}$F.

In some embodiments, each $R^A$ is independently H, F, Cl, Br, —CN, —$CH_3$, —$CF_3$, —$OCF_3$, or —$OCH_3$; each $R^{14}$ is independently H, F, Cl, Br, —CN, —$CH_3$, —$CF_3$, —$OCF_3$, or —$OCH_3$; r is 1.

In some embodiments, the compound of Formula (I) or Formula (II) has the structure of Formula (III):

Formula (III)

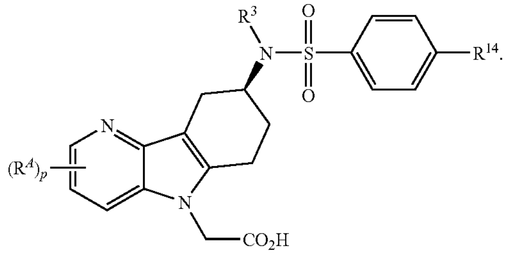

In some embodiments, $R^3$ is —$CH_3$; $R^{14}$ is F; p is 0.

In some embodiments, the compound of Formula (I) or Formula (II) has the structure of Formula (IV):

Formula (IV)

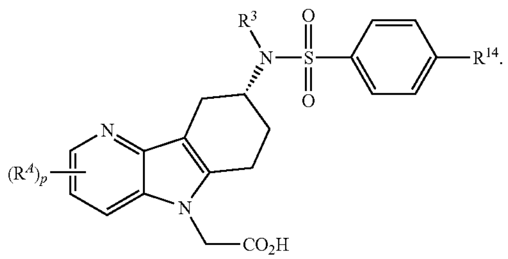

In some embodiments, $R^3$ is —$CH_3$; $R^{14}$ is F; p is 0.

In some embodiments, $R^2$ is as defined in Table 1. In some embodiments, $R^3$ is as defined in Table 1. In some embodiments, $R^{12}$ is as defined in Table 1.

Any combination of the groups described above for the various variables is contemplated herein. Throughout the specification, groups and substituents thereof are chosen by one skilled in the field to provide stable moieties and compounds.

Compounds of Formula (I) include, but are not limited to, those described in Table 1:

TABLE 1

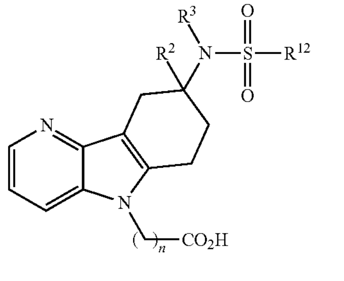

| Compound no. | $R^A$ | p | n | $R^2$ | $R^3$ | $R^{12}$ |
|---|---|---|---|---|---|---|
| 1 | H | 0 | 1 | H | H | 4-fluorophenyl |
| 2 | H | 0 | 1 | H | $-CH_3$ | 4-fluorophenyl |
| 3* | H | 0 | 1 | H | $-CH_3$ | 4-fluorophenyl |
| 4* | H | 0 | 1 | H | $-CH_3$ | 4-fluorophenyl |
| 5 | H | 0 | 2 | H | $-CH_3$ | 4-fluorophenyl |
| 6 | H | 0 | 1 | $CH_3$ | $-CH_3$ | 4-fluorophenyl |
| 7 | H | 0 | 1 | H | $-CH_3$ | 4-chlorophenyl |
| 8 | H | 0 | 1 | H | $-CH_3$ | 4-methoxyphenyl |
| 9 | H | 0 | 1 | H | $-CH_3$ | 4-cyanophenyl |
| 10 | H | 0 | 1 | H | $-CH_3$ | 4-trifluoromethylphenyl |
| 11 | H | 0 | 1 | H | $-CH_3$ | 3-fluorophenyl |
| 12 | H | 0 | 1 | H | $-CH_3$ | 2-fluorophenyl |
| 13 | H | 0 | 1 | H | $-CH_3$ | 3,4-difluorophenyl |
| 14 | H | 0 | 1 | H | $-CH_3$ | 6-methoxy-pyridin-3-yl |
| 15 | H | 0 | 1 | H | $-CH_3$ | 6-fluoro-pyridin-3-yl |
| 16 | H | 0 | 1 | H | $-CH_2CF_3$ | 4-fluorophenyl |

*single enantiomer

Compounds in Table 1 are named: {8-[(4-fluoro-benzenesulfonyl)-amino]-6,7,8,9-tetrahydro-pyrido[3,2-b]indol-5-yl}-acetic acid (Compound 1); {8-[(4-fluoro-benzenesulfonyl)-methyl-amino]-6,7,8,9-tetrahydro-pyrido[3,2-b]indol-5-yl}-acetic acid (Compound 2); (R)-{8-[(4-fluoro-benzenesulfonyl)-methyl-amino]-6,7,8,9-tetrahydro-pyrido[3,2-b]indol-5-yl}-acetic acid (Compound 3); (S)-{8-[(4-fluoro-benzenesulfonyl)-methyl-amino]-6,7,8,9-tetrahydro-pyrido[3,2-b]indol-5-yl}-acetic acid (Compound 4); {8-[(4-fluoro-benzenesulfonyl)-methyl-amino]-6,7,8,9-tetrahydro-pyrido[3,2-b]indol-5-yl}-propionic acid (Compound 5); {8-methyl-8-[(4-fluoro-benzenesulfonyl)-methyl-amino]-6,7,8,9-tetrahydro-pyrido[3,2-b]indol-5-yl}-acetic acid (Compound 6); {8-[(4-chloro-benzenesulfonyl)-methyl-amino]-6,7,8,9-tetrahydro-pyrido[3,2-b]indol-5-yl}-acetic acid (Compound 7); {8-[(4-methoxy-benzenesulfonyl)-methyl-amino]-6,7,8,9-tetrahydro-pyrido[3,2-b]indol-5-yl}-acetic acid (Compound 8); {8-[(4-cyano-benzenesulfonyl)-methyl-amino]-6,7,8,9-tetrahydro-pyrido[3,2-b]indol-5-yl}-acetic acid (Compound 9); {8-[(4-trifluoromethyl-benzenesulfonyl)-methyl-amino]-6,7,8,9-tetrahydro-pyrido[3,2-b]indol-5-yl}-acetic acid (Compound 10); {8-[(3-fluoro-benzenesulfonyl)-methyl-amino]-6,7,8,9-tetrahydro-pyrido[3,2-b]indol-5-yl}-acetic acid (Compound 11); {8-[(2-fluoro-benzenesulfonyl)-methyl-amino]-6,7,8,9-tetrahydro-pyrido[3,2-b]indol-5-yl}-acetic acid (Compound 12); {8-[(3,4-difluoro-benzenesulfonyl)-methyl-amino]-6,7,8,9-tetrahydro-pyrido[3,2-b]indol-5-yl}-acetic acid (Compound 13); {8-[(6-methoxy-pyridin-3-ylsulfonyl)-methyl-amino]-6,7,8,9-tetrahydro-pyrido[3,2-b]indol-5-yl}-acetic acid (Compound 14); {8-[(6-fluoro-pyridin-3-ylsulfonyl)-methyl-amino]-6,7,8,9-tetrahydro-pyrido[3,2-b]indol-5-yl}-acetic acid (Compound 15); and {8-[(4-fluoro-benzenesulfonyl)-(1,1,1-trifluoroeth-2-yl)-amino]-6,7,8,9-tetrahydro-pyrido[3,2-b]indol-5-yl}-acetic acid (Compound 16).

Further Forms of Compounds

In certain embodiments, compounds of Formula (I), (II), (III) and (IV) are prepared as pharmaceutically acceptable salts by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Pharmaceutically acceptable salts are also obtained by reacting a compound of Formula (I), (II), (III) or (IV) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like. In some embodiments, the pharmaceutically acceptable salt of the compound of Formula (I), (II), (III) or (IV) is the sodium salt of the compound of Formula (I), (II), (III) or (IV).

In other embodiments, compounds of Formula (I), (II), (III) and (IV) are prepared as a pharmaceutically acceptable salts by reacting the free acid form of the compound with a pharmaceutically acceptable inorganic or organic base, including, but not limited to organic bases such as ethanolamine, diethanolamine, triethanolamine, tromethamine, N-methylglucamine, and the like, or with an inorganic base such as aluminum hydroxide, calcium hydroxide, potassium hydroxide, sodium carbonate, sodium hydroxide, and the like.

Reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, and alcoholates are formed when the solvent is alcohol. Solvates of compounds of Formula (I), (II), (III) and (IV) are conveniently prepared or formed during the processes described herein. By way of example only, hydrates of compounds of Formula (I), (II), (III) and (IV) are conveniently prepared by recrystallization from an aqueous/organic solvent mixture, using organic solvents including, but not limited to, dioxane, tetrahydrofuran, ethanol, or methanol. In addition, the compounds provided herein can exist in unsolvated as well as solvated forms. In general, the solvated forms are considered equivalent to the unsolvated forms for the purposes of the compounds and methods provided herein.

In some embodiments, compounds of Formula (I), (II), (III) and (IV) are prepared as prodrugs. A "prodrug" refers to an agent that is converted into the parent drug in vivo.

In yet another embodiment, the compounds of Formula (I), (II), (III) and (IV) possess one or more stereocenters and each center exists independently in either the R or S configuration. The compounds presented herein include all diastereomeric, enantiomeric, and epimeric forms as well as the appropriate mixtures thereof. Stereoisomers are obtained, if desired, by methods such as, the separation of stereoisomers by chiral chromatographic columns or stereoselective synthesis.

The methods and formulations described herein include the use of N-oxides (if appropriate), crystalline forms (also known as polymorphs), or pharmaceutically acceptable salts of compounds having the structure of Formula (I), (II), (III) or (IV), as well as active metabolites of these compounds having the same type of activity. In some situations, compounds exist as tautomers.

In some embodiments, the compounds described herein exist as tautomers. All tautomers are intended to be within the scope of the molecular formulas described herein.

In some embodiments, compounds described herein are isotopically-labeled, which are identical to those recited in the various formulae and structures presented herein, but for the fact that one or more atoms are replaced by an atom having an atomic mass or mass number different from the atomic mass or mass number usually found in nature. In some embodiments, one or more hydrogen atoms are replaced with deuterium. In some embodiments, metabolic sites on the compounds described herein are deuterated. In some embodiments, substitution with deuterium affords certain therapeutic advantages resulting from greater metabolic stability, such as, for example, increased in vivo half-life or reduced dosage requirements.

Synthesis of Compounds

Compounds of Formula (I), (II), (III) and (IV) are prepared using synthetic methods known in the art and/or presented herein.

In some embodiments, compounds of Formula (I), (II), (III) and (IV) are prepared as outlined in Scheme 1.

Scheme 1

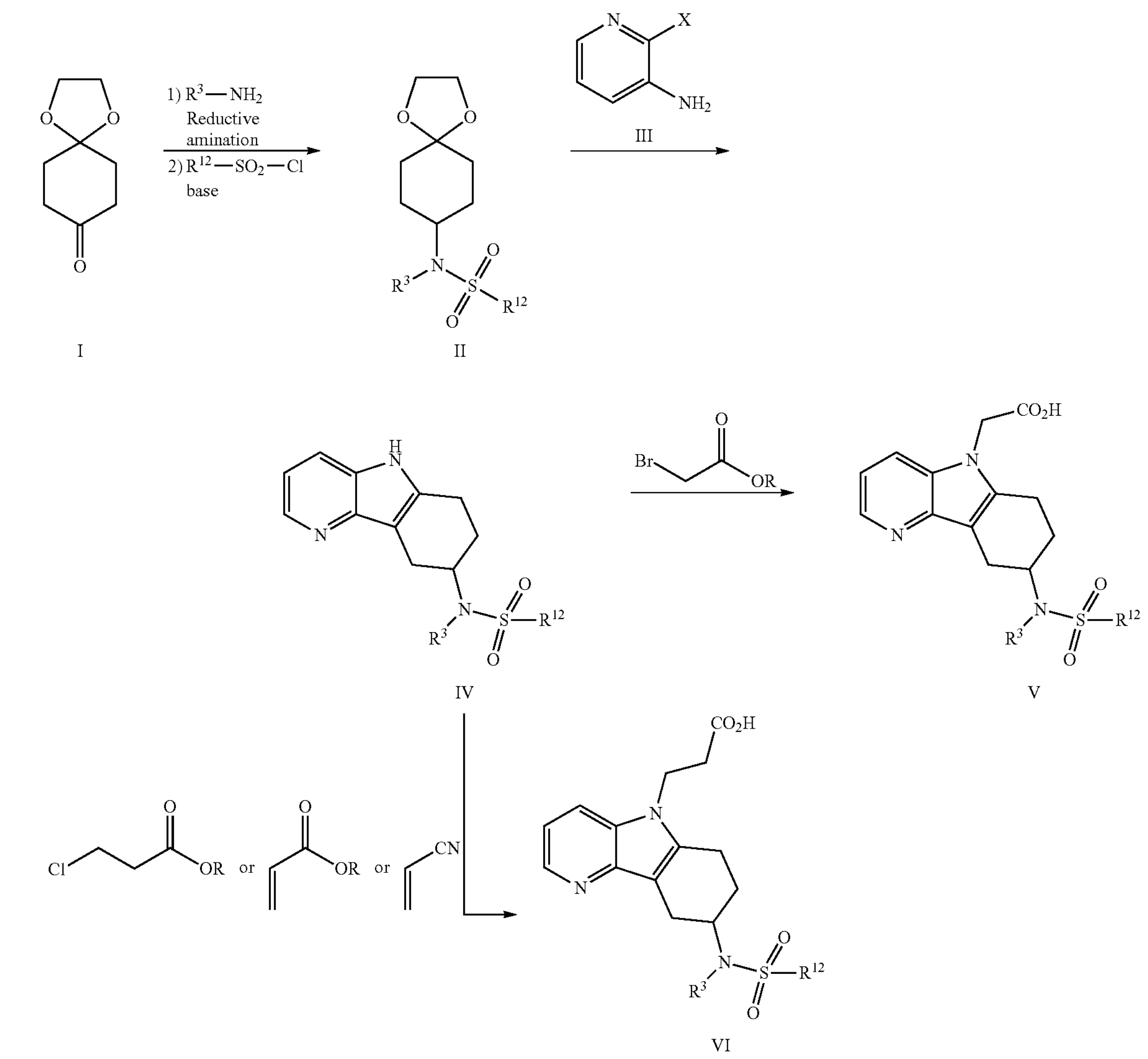

Ketone I is transformed to sulfonamide II using standard methods. In some embodiments, the reductive amination comprises a reducing agent. In some embodiments, the reducing agent is sodium cyanoborohydride or sodium triacetoxyborohydride. In some embodiments, the amine group is introduced via reductive amination of ketone I with benzylamine. The benzyl group is then removed under hydrogenation conditions. In some embodiments, the hydrogenation conditions comprise a palladium catalyst in a suitable solvent and in the presence of a hydrogen source. Following the removal of the benzyl group, the $R^3$ group is introduced by reaction of the sulfonamide with $R^3$—X in the presence of a suitable base and a suitable solvent, where X is a leaving group. In some embodiments, X is —Cl, —Br, —I, $—OSO_2CH_3$, $—OSO_2C_6H_5$, or $—OSO_2C_6H_4—CH_3$.

An intramolecular Heck reaction on the in situ imine resulting from condensation of ketal II with a 2-haloamino pyridine III provides the corresponding azaindole IV (Lachance, N.; April, M.; Joly, M.-A. *Synthesis,* 2005, 2571-2577). In some embodiments, the intramolecular Heck reaction is performed with a palladium catalyst. N-alkylation of the Heck product IV in a suitable solvent in the presence of a suitable base is followed by ester hydrolysis to provide the azaindole N-acetic acids V or azaindole N-propionic acids VI. In some embodiments, R is a $C_1$-$C_4$alkyl. In some embodiments, R is methyl or ethyl. Alternatively, Michael addition of IV to acrylonitrile or an alkyl acrylate followed by hydrolysis of the nitrile or ester provides the azaindole N-propionic acids VI.

In some embodiments, compounds of Formula (I), (II), (III) and (IV) are synthesized according to Schme 2.

Scheme 2

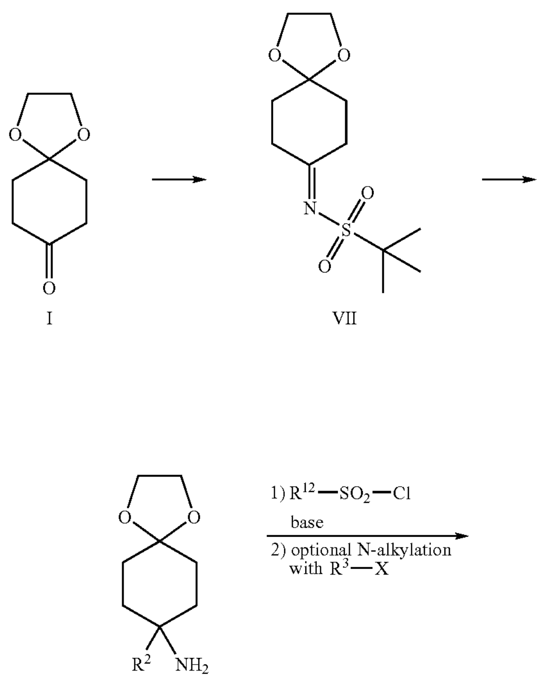

I

VII

VIII

-continued

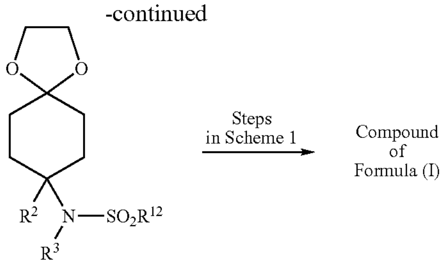

IX

Scheme 2 illustrates the introduction of substituents to the same carbon as the amine using 1,2-additions to sulfinyl ketimines VII, which are prepared from known procedures (Cogan and Ellman, *J. Am. Chem. Soc.,* 1999, 121, 268). Cleavage of the resulting sulfonamide provides amines VIII. Amines VIII are then further elaborated as described above in Scheme 1 to provide compounds of Formula (I), (II), (III) or (IV).

DEFINITIONS

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting.

"Alkoxy" refers to (alkyl)O—, where alkyl is as defined herein.

"Alkyl" refers to an aliphatic hydrocarbon group. The alkyl may be saturated or unsaturated, branched or straight chain. In one aspect, alkyl groups are selected from methyl, ethyl, propyl, iso-propyl, n-butyl, iso-butyl, sec-butyl, and tert-butyl.

"Cycloalkyl" refers to a monocyclic aliphatic, non-aromatic radical, wherein each of the atoms forming the ring (i.e. skeletal atoms) is a carbon atom. Cycloalkyl groups include, for example, cyclopropyl, cyclobutyl, cyclopentyl, and cyclohexyl.

"Halo", "halogen" or "halide" means fluoro, chloro, bromo or iodo.

"Fluoroalkyl" refers to an alkyl in which one or more hydrogen atoms are replaced by a fluorine atom. In one aspect, a fluoroalkyl is selected from $—CF_3$, $—CHF_2$, $—CH_2F$, $—CH_2CF_3$ and $—CF_2CF_3$.

"Fluoroalkoxy" refers to (fluoroalkyl)O—, where fluoroalkyl is as defined herein.

"Heteroalkyl" refers to an alkyl group in which one or more skeletal atoms of the alkyl are selected from an atom other than carbon, e.g., oxygen, nitrogen (e.g. NH or Nalkyl), or sulfur, or combinations thereof. In one aspect, heteroalkyl refers to an alkyl group in which one of the skeletal atoms of the alkyl is oxygen, nitrogen (e.g. NH or Nalkyl), or sulfur. In another aspect, heteroalkyl refers to an alkyl group in which one of the skeletal atoms of the alkyl is oxygen.

"Monocyclic heteroaryl" refers to aromatic heterocyclic rings that include 1 to 5 carbon atoms and at least one heteroatom selected from O, S, and N. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl.

"Bicyclic heteroaryl" refers to heterocyclic rings that include 5 to 9 carbon atoms and at least one heteroatom selected from O, S, and N. Bicyclic heteroaryls include quinolinyl, isoquinolinyl, indolyl, benzimidazolyl, benzofuranyl, cinnolinyl, indazolyl, indolizinyl, phthalazinyl, pteridinyl, purinyl, benzofurazanyl, benzothiophenyl, benzothiazolyl, benzoxazolyl, quinazolinyl, quinoxalinyl, naphthyridinyl, and furopyridinyl.

"6-Membered heteroaryl" includes pyridinyl, pyridazinyl, pyrimidinyl, pyrazinyl and triazinyl.

The term "optionally substituted" or "substituted" means that the referenced group may be substituted with one or more additional group(s) individually and independently selected from halogen, —OH, —CN, $C_1$-$C_4$alkyl, $C_1$-$C_4$fluoroalkyl, $C_1$-$C_4$alkoxy, $C_1$-$C_4$fluoroalkoxy, —$NH_2$, —NH($C_1$-$C_4$alkyl), —N($C_1$-$C_4$alkyl)$_2$, and $C_1$-$C_4$heteroalkyl. In some cases, the referenced substituted group is substituted with 1 or 2 of the aforementioned groups. For example, in some embodiments, a referenced substituted group is substituted with at least one group selected from halogen, —OH, —CN, —$CH_3$, —$CH_2CH_3$, —$CF_3$, —$OCH_3$, —$OCH_2CH_3$, and —$OCF_3$.

A "metabolite" of a compound disclosed herein is a derivative of that compound that is formed when the compound is metabolized. The term "active metabolite" refers to a biologically active derivative of a compound that is formed when the compound is metabolized.

"$PGD_2$-dependent" refers to conditions or disorders that would not occur, or would not occur to the same extent, in the absence of $PGD_2$. "$PGD_2$-mediated" refers to refers to conditions or disorders that might occur in the absence of $PGD_2$ but can occur in the presence of $PGD_2$.

"Effective amount" or "therapeutically effective amount," as used herein, refer to a sufficient amount of an agent or a compound being administered which will relieve to some extent one or more of the symptoms of the disease or condition being treated. An appropriate effective amount in any individual case may be determined using techniques, such as a dose escalation study.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "subject" or "patient" encompasses mammals. In one embodiment, the mammal is a human.

Pharmaceutical Composition/Formulation

Suitable routes of administration include, but are not limited to, oral, intravenous, rectal, aerosol, parenteral, ophthalmic, pulmonary, transmucosal, transdermal, vaginal, otic, nasal, intramuscular injection, subcutaneous injection, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner. In other embodiments, the compound as described herein is provided in the form of a rapid release formulation, in the form of an extended release formulation, or in the form of an intermediate release formulation. In yet other embodiments, the compound described herein is administered topically.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage F*orms *and* Drug Delivery Systems, Seventh Ed. (Lippincott Williams & Wilkins 1999).

A pharmaceutical composition refers to a mixture of a compound of Formula (I), (II), (III) or (IV) with other chemical components, such as carriers, stabilizers, diluents, dispersing agents, suspending agents, thickening agents, and/or excipients. In certain embodiments, the pharmaceutical composition facilitates administration of the compound to a mammal.

In some embodiments, compounds described herein are formulated for oral administration. The compounds described herein are formulated in oral dosage forms that include, by way of example only, tablets, powders, pills, dragees, capsules, liquids, gels, syrups, elixirs, slurries, suspensions and the like. In some embodiments, compounds described herein are formulated as tablets, powders, pills, or capsules. In some embodiments, compounds described herein are formulated as liquids, gels, syrups, elixirs, slurries, suspensions and the like.

In one embodiment, compounds of Formula (I), (II), (III) and (IV) are formulated in an aqueous solution. In specific embodiments, the aqueous solution is selected from, by way of example only, a physiologically compatible buffer, such as Hank's solution, Ringer's solution, or physiological saline buffer.

In other embodiments, compounds of Formula (I), (II), (III) and (IV) are formulated for transmucosal administration. In specific embodiments, transmucosal formulations include penetrants that are appropriate to the barrier to be permeated.

In still other embodiments wherein the compounds described herein are formulated for other parenteral injections, appropriate formulations include aqueous or nonaqueous solutions.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or pills. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

Oral dosage forms also include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds of Formula (I), (II), (III) and (IV) are administered topically. Topically administrable compositions include solutions, suspensions, lotions, gels, pastes, medicated sticks, balms, creams or ointments.

In other embodiments, the compounds of Formula (I), (II), (III) and (IV) are formulated for administration by inhalation. Various forms suitable for administration by inhalation include, but are not limited to, aerosols, mists or powders.

The active ingredient in the pharmaceutical compositions is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions comprising the compounds described herein are administered to a patient susceptible to or otherwise at risk of a particular disease, disorder or condition. In this use, the precise amounts also depend on the patient's state of health, weight, and the like.

The amount of a given agent that corresponds to such an amount varies depending upon factors such as the particular compound, disease or condition and its severity, the identity (e.g., weight) of the mammal in need of treatment, but can nevertheless be determined according to the particular circumstances surrounding the case, including, e.g., the specific agent being administered, the route of administration, the condition being treated, and the mammal being treated. Doses employed for adult human treatment are typically in the range of 0.02-5000 mg per day, 0.5-1500 mg per day, or 1-500 mg per day. In one embodiment, the dose is presented in a single dose or in divided doses administered at appropriate intervals, for example as two, three, four or more sub-doses per day.

In one embodiment, the daily dosages appropriate for the compound of Formula (I), (II), (III) or (IV) are from about 0.01 to about 10 mg/kg per body weight. In certain embodiments, suitable unit dosage forms for oral administration comprise from about 1 to 500 mg active ingredient. In other embodiments, the daily dosage or the amount of active in the dosage form are lower or higher than the ranges indicated herein.

In certain instances, it is appropriate to administer at least one compound of Formula (I), (II), (III) or (IV) in combination with another therapeutic agent. In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

In some embodiments, compounds of Formula (I), (II), (III) or (IV) are administered chronically. In some embodiments, compounds of Formula (I), (II), (III) or (IV) are administered intermittently (e.g. drug holiday that includes a period of time in which the compound is not administered or is administered in a reduced amount). In some embodiments, compounds of Formula (I), (II), (III) or (IV) are administered in cycles that include: (a) a first period that includes daily administration of the compound of Formula (I); followed by (b) a second period that includes a dose reduction of the daily amount of compound of Formula (I), (II), (III) or (IV) that is administered. In some embodiments, the compound of Formula (I), (II), (III) or (IV) is not administered in the second period. In some embodiments, the duration of the first and second periods, as well as the dose amounts are determined using methods described herein or known in the art.

EXAMPLES

These examples are provided for illustrative purposes only and not to limit the scope of the claims provided herein.

Example 1

Synthesis of {8-[(4-fluoro-benzenesulfonyl)-methyl-amino]-6,7,8,9-tetrahydro-pyrido[3,2-b]indol-5-yl}-acetic acid Step 1: A solution of 1,4-dioxa-spiro[4.5]decan-8-one (3.1 g, 20 mmol) and $CH_2Cl_2$ (50 mL) was stirred with methylamine (15 mL, 30 mmol, 2.0M solution in THF), sodium cyanoborohydride (1.3 g, 20 mmol), and acetic acid (0.1 mL) at room temperature. After 8 hours, the reaction mixture was washed with water (50 mL) and concentrated. The residue was purified by flash chromatography to afford 1.5 g of (1,4-dioxa-spiro[4.5]dec-8-yl)-methyl-amine as an oil.

Step 2: A solution of (1,4-dioxa-spiro[4.5]dec-8-yl)-methyl-amine (1.5 g, 9 mmol), $CH_2Cl_2$ (50 mL), and $Et_3N$ (1.7 mL, 12 mmol) was stirred with 4-fluorobenzene sulfonyl chloride (1.7 g, 9 mmol) at room temperature. After 1 hour, the reaction mixture was concentrated and the residue purified by flash chromatography on silica gel to afford 2.1 g of N-(1,4-dioxa-spiro[4.5]dec-8-yl)-4-fluoro-N-methyl-benzenesulfonamide. Mass spectrometric data $[M+H]^+$=330.

Step 3: A solution of 2-bromo-3-aminopyridine (2.1 g, 12.2 mmol), N-(1,4-dioxa-spiro[4.5]dec-8-yl)-4-fluoro-N-methyl-benzenesulfonamide (4.8 g, 14.7 mmol), tetrakis(triphenylphosphine)palladium(0) (700 mg, 0.6 mmol), and pyridine (8 mL) were combined in a vial. The vial was heated by microwave irradiation at 160° C. for 60 min. The reaction mixture is poured into water (100 mL) and the resulting solid is filtered and dried under vacuum to 2.8 g of 4-fluoro-N-methyl-N-(6,7,8,9-tetrahydro-5H-pyrido[3,2-b]indol-8-yl)-benzenesulfonamide as a yellow solid. Mass spectrometric data $[M+H]^+=360$ Step 4: A solution of 4-fluoro-N-methyl-N-(6,7,8,9-tetrahydro-5H-pyrido[3,2-b]indol-8-yl)-benzenesulfonamide (2.8 g, 7.8 mmol) and DMF (22 mL) was cooled to 0° C. Sodium hydride (340 mg, 8.6 mmol, 60% dispersion in mineral oil) was added at 0° C. and after 30 min, tert-butylbromoacetate (1.3 mL, 8.9 mmol) was added at 0° C. After 1 hour, MeOH was added and the reaction mixture was filtered. The organic layer was concentrated and the residue purified by reverse phase preparative HPLC to afford 700 mg of {8-[(4-fluoro-benzenesulfonyl)-methyl-amino]-6,7,8,9-tetrahydro-pyrido[3,2-b]indol-5-yl}-acetic acid tert-butyl ester. Mass spectrometric data $[M+H]^+=474$.

Step 5: A solution of {8-[(4-fluoro-benzenesulfonyl)-methyl-amino]-6,7,8,9-tetrahydro-pyrido[3,2-b]indol-5-yl}-acetic acid tert-butyl ester (43 mg, 0.9 mmol) was dissolved in THF (1 mL), MeOH (1 mL) and 1N NaOH (0.2 mL). After 24 hours, the reaction mixture was neutralized with 1N HCl and concentrated to afford 40 mg of {8-[(4-fluoro-benzenesulfonyl)-methyl-amino]-6,7,8,9-tetrahydro-pyrido[3,2-b]indol-5-yl}-acetic acid. Mass spectrometric data $[M+H]^+=418$.

Enantiomer separation of {8-[(4-fluoro-benzenesulfonyl)-methyl-amino]-6,7,8,9-tetrahydro-pyrido[3,2-b]indol-5-yl}-acetic acid Racemic {8-[(4-fluoro-benzenesulfonyl)-methyl-amino]-6,7,8,9-tetrahydro-pyrido[3,2-b]indol-5-yl}-acetic acid, tert-butyl ester was separated on a chiracel AS column utilizing a gradient of 95/5 hexanes/ethanol and a flow rate of 20 mL/min. The first peak off the column was collected and the fractions concentrated. The residue was combined with TFA (0.5 mL) and $CH_2Cl_2$ (1.2 ml). After 8 hours, the mixture was concentrated to afford 138 mg of {8-[(4-fluoro-benzenesulfonyl)-methyl-amino]-6,7,8,9-tetrahydro-pyrido[3,2-b]indol-5-yl}-acetic acid, trifluoroacetate salt (Enantiomer A). Mass spectrometric data $[M+H]^+=418$. Based on analogy to ramatroban, Enantiomer A is designated as the R-enantiomer.

The second peak off the column was collected and the fractions concentrated. The residue was combined with TFA (0.5 mL) and $CH_2Cl_2$ (1.2 ml). After 8 hours, the mixture was concentrated to afford 150 mg of {8-[(4-fluoro-benzenesulfonyl)-methyl-amino]-6,7,8,9-tetrahydro-pyrido[3,2-b]indol-5-yl}-acetic acid, trifluoroacetate salt (Enantiomer B). Mass spectrometric data $[M+H]^+=418$. Based on analogy to ramatroban, Enantiomer B is designated as the S-enantiomer.

Example 2a $DP_2$/CRTH2 Binding Assay

The ability of a compound to bind to the human $DP_2$ receptor is assessed via a radioligand binding assay using $[^3H]PGD_2$. HEK293 cells stably expressing recombinant human $DP_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 μg protein/well) are incubated in 96-well plates with 1 nM $[^3H]PGD_2$ and test compound in Assay Buffer (50 mM Hepes, 10 mM $MnCl_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polyethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM $PGD_2$. $IC_{50}$s were determined using GraphPad prism analysis of drug titration curves. Compounds tested had an $IC_{50}$ of less than 5 micromolar in this assay.

Example 2b

GTPγS Binding Assay

The ability of a compound to inhibit binding of GTP to $DP_2$ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 μg per well) are incubated in 96-well plates with 0.05 nM $[^{35}S]$-GTPγS, 80 nM $PGD_2$, 5 μM GDP, and test compound in Assay Buffer (50 mM Hepes, pH 7.4, 100 mM NaCl, 5 mM $MgCl_2$ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM $PGD_2$). $IC_{50}$s were determined using Graphpad prism analysis of drug titration curves.

Example 2c

Whole Blood Esoinophil Shape Change Assay

Blood is drawn from consenting human volunteers in EDTA vacutainer tubes and used within 1 hr of draw. A 98 μl aliquot of blood is mixed with 2 μl of test compound (in 50% DMSO) in 1.2 ml polypropylene tubes. The blood is vortexed and incubated at 37° C. for 15 minutes. 5 μl of 1 μM $PGD_2$ in PBS is added for a final concentration of 50 nM and the tubes briefly vortexed. The reactions are incubated for exactly 5 minutes at 37° C. and then terminated by placing the tubes on ice and immediately adding 250 μl of ice-cold 1:4 diluted Cytofix (BD Biosciences). The reactions are transferred to 12×75 mM polystyrene round bottom tubes and the red blood cells lysed by the addition of 3 ml ammonium chloride lysing solution (150 mM $NH_4Cl$, 10 mM $KHCO_3$, 0.1 mM EDTA disodium salt) and incubation at room temperature for 15 minutes. The cells are pelleted by spinning at 1300 rpm for 5 minutes at 4° C. and washed once with 3 ml ice-cold PBS. The cells are resuspended in 0.2 ml of ice-cold 1:4 diluted Cytofix (BD Biosciences) and analyzed on a FACSCalibur (BD Biosciences) within 2 hours. Eosinophils were gated on the basis of autofluorescence in the FL2 channel and shape change on 500 eosinophils was assayed by forward scatter and side scatter analysis. The specific change in shape induced by $PGD_2$ was calculated as the difference between the percentage of high forward scatter eosinophils in the presence and absence of $PGD_2$. $IC_{50}$s were determined using Graphpad Prism® analysis of drug titration curves.

Example 2d $DP_1$ Binding Assay

The ability of a compound to bind to the human DP1 receptor was evaluated via a radioligand membrane binding assay using the $DP_1$ selective synthetic ligand [$^3$H] BWA868C. Packed human platelets (Biological Specialty Corporation), were resuspended in 6 volumes of Hepes/HBSS buffer (10 mM Hepes, 1 mM DTT in Hanks Balanced Salt Solution (HBSS), lysed and centrifuged at 75,000×g to pellet the membranes. Membranes were resuspended in Hepes/HBSS buffer to approximately 12 mg protein/ml. Membranes (20 μg protein/well) are incubated in 96-well plates with 2 nM [$^3$H]BWA868C and test compound in Assay Buffer (50 mM Hepes, 10 mM $MnCl_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polyethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM BW A868C. $IC_{50}$s were determined using GraphPad prism analysis of drug titration curves.

Biological data for illustrative compounds disclosed herein is presented in Table 2.

TABLE 2

Representative Biological Data

| Compound Number | hDP2 (μM) |
|---|---|
| {8-[(4-fluoro-benzenesulfonyl)-methyl-amino]-6,7,8,9-tetrahydro-pyrido[3,2-b]indol-5-yl}-acetic acid | A |
| {8-[(4-fluoro-benzenesulfonyl)-methyl-amino]-6,7,8,9-tetrahydro-pyrido[3,2-b]indol-5-yl}-acetic acid, Enantiomer A | A |
| {8-[(4-fluoro-benzenesulfonyl)-methyl-amino]-6,7,8,9-tetrahydro-pyrido[3,2-b]indol-5-yl}-acetic acid, Enantiomer B | B |
| Ramatroban | B |

A = less than 0.1 μM; B = greater than 0.1 μM.

Example 3

Mouse Allergic Rhinitis Model

The compounds ability to inhibit allergen-induced sneezing and nasal rubbing is assessed using a mouse model of allergic rhinitis. Methods were adapted from those detailed in Nakaya, M., et al. 2006, *Laboratory Investigation,* 86:917-926. Female BALB/c mice (20-25 g) are immunized by an intraperitoneal injection (i.p.) of 10 μg ovalbumin (OVA) complexed with alum in a volume 0.2 mL on days 0 and 7. Fourteen days later (day 21) mice are challenged intranasally with 20 μl of a 10 mg/mL solution of OVA. The challenge period occurs daily from days 21 to day 23. Mice (5-7/group) are randomly assigned to receive either compound or vehicle and are treated by oral gavage 1 hour prior to OVA challenge. The number of sneezes and nasal rubs are counted by an independent blinded observe during a period of 8 minutes immediately following OVA challenge on days 21, 23 and 25. A significant increase in allergen-induced sneezing and nasal rubbing occurs over the 3-day challenge period. Inhibition of this effect by select compounds is determined statistically using Graphpad prism.

In the mouse model of allergic rhinitis, {8-[(4-fluoro-benzenesulfonyl)-methyl-amino]-6,7,8,9-tetrahydro-pyrido[3,2-b]indol-5-yl}-acetic acid (10 mg/kg administered as the sodium salt) significantly reduced (approximately 40-50%) the sneezing and nasal rubs in the mice treated with compound versus those mice treated with vehicle. Plasma concentrations of the compound from a group of mice revealed a Cmax of 770 nM and a Cmin of 120 nM at 8 hours.

Example 4

Guinea Pig IV-DKPGD2-Induced Peripheral Blood Leukocyte Influx

The compounds ability to inhibit leukocyte migration in vivo was assessed using intravenous injection of 13,14-dihydro-15-keto-prostaglandin D2 (DK-PGD2). Methods were adapted from those detailed Shichijo et al., 2003*, Journal of Pharmacology and Experimental Therapeutics,* 307:518-525. Male Hartley guinea pigs were immunized with ovalbumin (OVA) on day 0 by intraperitoneal (IP) injection of 1 ml of a 100 μg/ml solution in Imject Alum. They were then used in the DK-PGD2 procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-PGD2 (1 mg/kg, IV). Thirty minutes after IV administration, blood was collected via the marginal ear vein into EDTA tubes for cell analysis. A sample of 10 μl blood was lysed in 190 μl water followed by a further 20-fold dilution in PBS. A 10 μl fraction was mixed with equal parts trypan blue and loaded on a hemocytometer. Cells were visualized at a magnification of 40× using a LabPro light microscope and total cells were counted and recorded. Cells are expressed as total cells×$10^8$ per ml of blood. Statistical significance of cell influx by select compounds is determined using Graphpad prism.

Example 5

Clinical Trials in Humans

Study 1: Clinical Trial Evaluating Effect of Compound of Formula (I), (II), (III) or (IV) on Ex Vivo PGD2-Induced Blood Eosinophil Shape Change In this double-blind, randomized, placebo-controlled, single ascending dose study of Compound of Formula (I), (II), (III) or (IV) in healthy volunteers the inhibition of ex vivo $PGD_2$-induced blood eosinophil shape change is determined to show proof of biochemical mechanism of DP2 receptor antagonism. Eight subjects (6 active, 2 placebo) per dose level are used. Pre dose blood is drawn and challenged with $PGD_2$ to determine baseline shape change as described above in Example 2. At varying times after dosing blood is drawn for both pharmacokinetic analyses of drug concentration in blood, and also for $PGD_2$ challenge and eosinophil shape change determination. The extent of receptor blockage is determined from the relationship between drug blood concentration and percentage inhibition of eosinophil shape change.

Study 2: Clinical Trial Evaluating Effect of Compound of Formula (I), (II), (III) or (IV) on Allergen-Induced Nasal Symptoms and Inflammatory and Allergic Biomarkers In this double-blind, randomized, placebo-controlled study of compound of Formula (I), (II), (III) or (IV) in individuals with allergic rhinitis the inhibition of nasal symptoms and allergic biomarkers is determined following nasal challenge with appropriate allergen. Fifteen subjects (10 active, 5 placebo) are used. Subjects are dosed for 7 days with either placebo or an amount of compound of Formula (I), (II), (III) or (IV) that results in complete DP2 receptor block in an ex vivo $PGD_2$-induced blood eosinophil shape change pharmacodynamic study as described above. On day 7 subjects undergo nasal allergen challenge (2 hours post-dose) and early allergic response (0.25-1.0 hr) and late allergic response (4-24 hr) are evaluated as an increase from baseline for treated vs placebo. In addition changes in inflammatory cell differentials, Th2 cytokines and other inflammatory markers are determined as increase from baseline for treated vs. placebo.

Compound of Formula (I), (II), (III) or (IV) Assay

The plasma concentrations of compound of Formula (I), (II), (III) or (IV) are determined by gas chromatography, giving a detection limit of 1 ng·ml-1 (Ritter W. Determination of BAY u 3405, a novel thromboxane antagonist, in plasma and urine by HPLC and GC. In: Reid E, Wilson I D, eds. Bioanalytical Approaches for Drugs, Including Anti-asthmatics and Metabolites. Methodological Surveys in Biochemistry and Analysis, 1992; 22: 211-216).

Study 3—Vienna Challenge Chamber Study

Study design: The study is a randomised, double blind, placebo controlled, two way crossover evaluation of compound of Formula (I), (II), (III) or (IV), given orally for eight days. There is a screening period of one week and a washout period of three weeks between the two treatment periods.

There is a follow up one week after the last dose of study drug. The group of patients who receive the study drug for the first treatment period and placebo for the second are designated group A, while the group of patients who receive placebo for the first treatment period and the study drug for the second treatment period are designated group B.

Treatment plan and methods: The subjects undergo a complete screening assessment to determine a baseline response to allergens. This screening assessment takes place one week prior to the start of dosing.

Subjects commence dosing with compound of Formula (I), (II), (III) or (IV) or placebo on Day 1 of each treatment period of the study. Adverse events, total nasal symptom score and concomitant medications are noted.

Subjects report back to the clinic on Day 2 of each treatment period for a 6 hour allergen challenge. The following measurements are obtained:

- Total nasal symptom score (TNSS) (obstruction, rhinorrhoea, itch, sneeze) with each symptom scored on a categorical scale from 0 to 3 pre-challenge, every 15 mins from 0 to 6 h post-start of challenge
- Eye symptom score (watery eyes, itchy eyes, red eyes) with each symptom scored on a categorical scale from 0 to 3 pre-challenge, every 15 mins from 0 to 6 h post-start of challenge
- Other symptoms (cough, itchy throat, itchy ears) with each symptom scored on a categorical scale from 0 to 3 pre-challenge and every 15 mins from 0 to 6 h post-start of challenge Subjects report back to the clinic on Day 8 of each treatment period for a 6 hour allergen challenge and the measurements obtained on Day 2 are repeated.

A final follow-up visit is conducted one week after the last dose of test article in Treatment Period 2.

Example 6a

Parenteral Composition

To prepare a parenteral pharmaceutical composition suitable for administration by injection, 100 mg of a water-soluble salt of a compound of Formula (I), (II), (III) or (IV) is dissolved in sterile water and then mixed with 10 mL of 0.9% sterile saline. The mixture is incorporated into a dosage unit form suitable for administration by injection.

Example 6b

Oral Composition

To prepare a pharmaceutical composition for oral delivery, 100 mg of a compound of Formula (I), (II), (III) or (IV) is mixed with 750 mg of starch. The mixture is incorporated into an oral dosage unit for, such as a hard gelatin capsule, which is suitable for oral administration.

Example 6c

Sublingual (Hard Lozenge) Composition

To prepare a pharmaceutical composition for buccal delivery, such as a hard lozenge, mix 100 mg of a compound of Formula (I), (II), (III) or (IV) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 6d

Fast-Disintegrating Sublingual Tablet

A fast-disintegrating sublingual tablet is prepared by mixing 48.5% by weigh of a compound of Formula (I), (II), (III) or (IV), 44.5% by weight of microcrystalline cellulose (KG-802), 5% by weight of low-substituted hydroxypropyl cellulose (50 μm), and 2% by weight of magnesium stearate. Tablets are prepared by direct compression (*AAPS Pharm Sci Tech.* 2006; 7(2):E41). The total weight of the compressed tablets is maintained at 150 mg. The formulation is prepared by mixing the amount of compound of Formula (I), (II), (III) or (IV) with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 6e

Inhalation Composition

To prepare a pharmaceutical composition for inhalation delivery, 20 mg of a compound of Formula (I), (II), (III) or (IV) is mixed with 50 mg of anhydrous citric acid and 100 mL of 0.9% sodium chloride solution. The mixture is incorporated into an inhalation delivery unit, such as a nebulizer, which is suitable for inhalation administration.

Example 6f

Rectal Gel Composition

To prepare a pharmaceutical composition for rectal delivery, 100 mg of a compound of Formula (I), (II), (III) or (IV) is mixed with 2.5 g of methylcelluose (1500 mPa), 100 mg of methylparaben, 5 g of glycerin and 100 mL of purified water. The resulting gel mixture is then incorporated into rectal delivery units, such as syringes, which are suitable for rectal administration.

Example 6g

Topical Gel Composition

To prepare a pharmaceutical topical gel composition, 100 mg of a compound of Formula (I), (II), (III) or (IV) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topical administration.

Example 6h

Ophthalmic Solution Composition

To prepare a pharmaceutical ophthalmic solution composition, 100 mg of a compound of Formula (I), (II), (III) or (IV) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 6i

Nasal Spray Solution

To prepare a pharmaceutical nasal spray solution, 10 g of a compound of Formula (I), (II), (III) or (IV) is mixed with 30 mL of a 0.05M phosphate buffer solution (pH 4.4). The solution is placed in a nasal administrator designed to deliver 100 μl of spray for each application.

The examples and embodiments described herein are for illustrative purposes only and various modifications or changes suggested to persons skilled in the art are to be included within the spirit and purview of this application and scope of the appended claims.

What is claimed is:

1. A compound having the structure of Formula (I), or a pharmaceutically acceptable salt, or N-oxide thereof:

Formula (I)

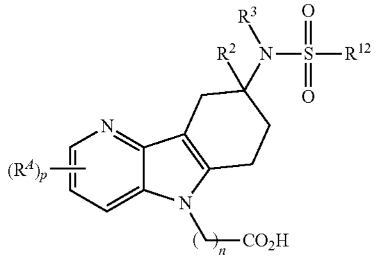

wherein, each $R^A$ is independently H, F, Cl, Br, I, —CN, —$NO_2$, $C_1$-$C_4$alkyl, $C_1$-$C_4$fluoroalkyl, $C_1$-$C_4$fluoroalkoxy, $C_1$-$C_4$alkoxy, or $C_1$-$C_4$heteroalkyl;

$R^2$ is H or $C_1$-$C_4$alkyl;

$R^3$ is H, $C_1$-$C_4$alkyl, $C_1$-$C_4$fluoroalkyl or -$L^3$-$X^3$;

-$L^3$- is —$C_1$-$C_4$alkylene-;

—$X^3$ is H, F, —CN, —$CO_2R^{13}$, —C(═O)N($R^{13}$)$_2$, tetrazolyl, or —OH;

$R^{12}$ is $C_1$-$C_6$alkyl, $C_1$-$C_6$haloalkyl, $C_1$-$C_6$heteroalkyl, a substituted or unsubstituted phenyl, a substituted or unsubstituted naphthyl, a substituted or unsubstituted monocyclic heteroaryl or a substituted or unsubstituted bicyclic heteroaryl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, $C_1$-$C_4$alkyl, $C_1$-$C_4$fluoroalkyl, $C_1$-$C_4$alkoxy, $C_1$-$C_4$fluoroalkoxy, or $C_1$-$C_4$heteroalkyl;

each $R^{13}$ is independently H, $C_1$-$C_4$alkyl, or a substituted or unsubstituted phenyl;

n is 1 or 2;

p is 0, 1 or 2.

2. The compound of claim 1, or a pharmaceutically acceptable salt, or N-oxide thereof, wherein:

$R^2$ is H or —$CH_3$;

$R^3$ is H, —$CH_3$, —$CH_2CH_3$, or —$CH_2CF_3$;

n is 1.

3. The compound of claim 2, or a pharmaceutically acceptable salt, or N-oxide thereof, wherein:

$R^2$ is H;

$R^{12}$ is a substituted or unsubstituted phenyl, or a substituted or unsubstituted 6-membered monocyclic heteroaryl, where if $R^{12}$ is substituted then $R^{12}$ is substituted with 1 or 2 $R^{14}$; each $R^{14}$ is independently H, F, Cl, Br, I, —CN, —$NH_2$, —OH, —NH($CH_3$), —N($CH_3$)$_2$, —$CH_3$, —$CF_3$, —$OCH_3$, or —$OCF_3$.

4. The compound of claim 3, or a pharmaceutically acceptable salt, or N-oxide thereof, wherein the compound of Formula (I) has the structure of Formula (II):

Formula (II)

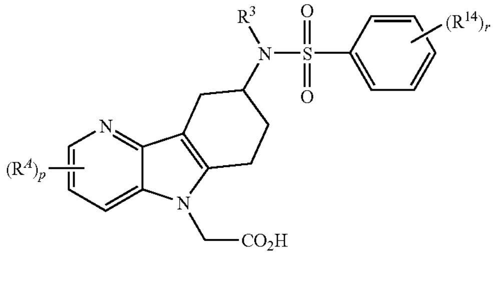

wherein:

r is 0, 1 or 2.

5. The compound of claim 4, or a pharmaceutically acceptable salt, or N-oxide thereof, wherein:

each $R^A$ is independently H, F, Cl, Br, —CN, —$CH_3$, —$CF_3$, —$OCF_3$, or —$OCH_3$;

each $R^{14}$ is independently H, F, Cl, Br, —CN, —$CH_3$, —$CF_3$, —$OCF_3$, or —$OCH_3$;

r is 1.

6. The compound of claim 5, or a pharmaceutically acceptable salt, or N-oxide thereof, wherein the compound of Formula (II) has the structure of Formula (III):

Formula (III)

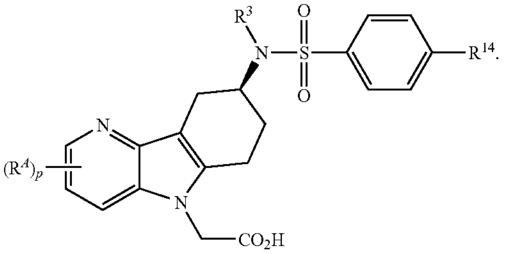

7. The compound of claim 6, or a pharmaceutically acceptable salt, or N-oxide thereof, wherein:

$R^3$ is —$CH_3$;

$R^{14}$ is F;

p is 0.

8. The compound of claim 5, or a pharmaceutically acceptable salt, or N-oxide thereof, wherein the compound of Formula (II) has the structure of Formula (IV):

Formula (IV)

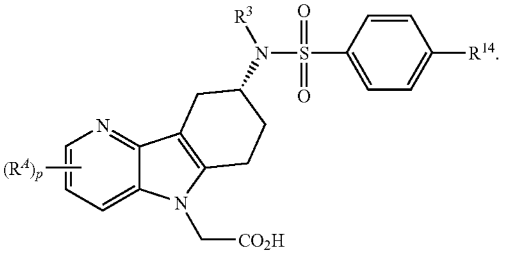

9. The compound of claim 8, or a pharmaceutically acceptable salt, or N-oxide thereof, wherein:

$R^3$ is —$CH_3$;

$R^{14}$ is F;

p is 0.

10. The compound of claim 1 selected from:

{8-[(4-fluoro-benzenesulfonyl)-amino]-6,7,8,9-tetrahydro-pyrido[3,2-b]indol-5-yl}-acetic acid;

{8-[(4-fluoro-benzenesulfonyl)-methyl-amino]-6,7,8,9-tetrahydro-pyrido[3,2-b]indol-5-yl}-acetic acid;

(R)-{8-[(4-fluoro-benzenesulfonyl)-methyl-amino]-6,7,8,9-tetrahydro-pyrido[3,2-b]indol-5-yl}-acetic acid;

(S)-{8-[(4-fluoro-benzenesulfonyl)-methyl-amino]-6,7,8,9-tetrahydro-pyrido[3,2-b]indol-5-yl}-acetic acid;

{8-[(4-fluoro-benzenesulfonyl)-methyl-amino]-6,7,8,9-tetrahydro-pyrido[3,2-b]indol-5-yl}-propionic acid;

{8-methyl-8-[(4-fluoro-benzenesulfonyl)-methyl-amino]-6,7,8,9-tetrahydro-pyrido[3,2-b]indol-5-yl}-acetic acid;

{8-[(4-chloro-benzenesulfonyl)-methyl-amino]-6,7,8,9-tetrahydro-pyrido[3,2-b]indol-5-yl}-acetic acid;

{8-[(4-methoxy-benzenesulfonyl)-methyl-amino]-6,7,8,9-tetrahydro-pyrido[3,2-b]indol-5-yl}-acetic acid;

{8-[(4-cyano-benzenesulfonyl)-methyl-amino]-6,7,8,9-tetrahydro-pyrido[3,2-b]indol-5-yl}-acetic acid;

{8-[(4-trifluoromethyl-benzenesulfonyl)-methyl-amino]-6,7,8,9-tetrahydro-pyrido[3,2-b]indol-5-yl}-acetic acid;

{8-[(3-fluoro-benzenesulfonyl)-methyl-amino]-6,7,8,9-tetrahydro-pyrido[3,2-b]indol-5-yl}-acetic acid;

{8-[(2-fluoro-benzenesulfonyl)-methyl-amino]-6,7,8,9-tetrahydro-pyrido[3,2-b]indol-5-yl}-acetic acid;

{8-[(3,4-difluoro-benzenesulfonyl)-methyl-amino]-6,7,8,9-tetrahydro-pyrido[3,2-b]indol-5-yl}-acetic acid;

{8-[(6-methoxy-pyridin-3-ylsulfonyl)-methyl-amino]-6,7,8,9-tetrahydro-pyrido[3,2-b]indol-5-yl}-acetic acid;

{8-[(6-fluoro-pyridin-3-ylsulfonyl)-methyl-amino]-6,7,8,9-tetrahydro-pyrido[3,2-b]indol-5-yl}-acetic acid; and {8-[(4-fluoro-benzenesulfonyl)-(1,1,1-trifluoroeth-2-yl)-amino]-6,7,8,9-tetrahydro-pyrido[3,2-b]indol-5-yl}-acetic acid;

or a pharmaceutically acceptable salt, or N-oxide thereof.

11. A pharmaceutical composition comprising a therapeutically effective amount of a compound of claim 1, or pharmaceutically acceptable salt, or N-oxide thereof, and at least one pharmaceutically acceptable inactive ingredient selected from pharmaceutically acceptable diluents, pharmaceutically acceptable excipients, and pharmaceutically acceptable carriers.

12. The pharmaceutical composition of claim 11, wherein:

(a) the pharmaceutical composition is formulated for intravenous injection, oral administration, inhalation, nasal administration, topical administration, ophthalmic administration or otic administration; or (b) the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

* * * * *